(12) United States Patent
Eriksson et al.

(10) Patent No.: US 9,376,409 B2
(45) Date of Patent: Jun. 28, 2016

(54) METHODS FOR MAKING OXETAN-3-YLMETHANAMINES

(71) Applicant: Boehringer Ingelheim International GmbH, Ingelheim am Rhein (DE)

(72) Inventors: Magnus Carl Arne Eriksson, Brookfield, CT (US); Suresh R. Kapadia, Danbury, CT (US); Jonathan Timothy Reeves, New Milford, CT (US); Xingzhong Zeng, New Milford, CT (US)

(73) Assignee: BOEHRINGER INGELHEIM INTERNATIONAL GMBH, Ingelheim am Rhein (DE)

( * ) Notice: Subject to any disclaimer, the term of this patent is extended or adjusted under 35 U.S.C. 154(b) by 0 days.

(21) Appl. No.: 14/399,343

(22) PCT Filed: May 1, 2013

(86) PCT No.: PCT/US2013/038969
§ 371 (c)(1),
(2) Date: Nov. 6, 2014

(87) PCT Pub. No.: WO2013/169531
PCT Pub. Date: Nov. 14, 2013

(65) Prior Publication Data
US 2015/0119589 A1  Apr. 30, 2015

Related U.S. Application Data

(60) Provisional application No. 61/644,476, filed on May 9, 2012.

(51) Int. Cl.
| | | |
|---|---|---|
| C07D 305/06 | (2006.01) |
| C07C 215/10 | (2006.01) |
| C07C 227/10 | (2006.01) |
| C07C 229/24 | (2006.01) |
| C07C 213/00 | (2006.01) |
| C07C 215/28 | (2006.01) |
| C07C 229/34 | (2006.01) |

(52) U.S. Cl.
CPC ............ *C07D 305/06* (2013.01); *C07C 213/00* (2013.01); *C07C 215/10* (2013.01); *C07C 215/28* (2013.01); *C07C 227/10* (2013.01); *C07C 229/24* (2013.01); *C07C 229/34* (2013.01)

(58) Field of Classification Search
None
See application file for complete search history.

(56) References Cited

U.S. PATENT DOCUMENTS

| | | | |
|---|---|---|---|
| 6,894,189 B2 | 5/2005 | Senanayake et al. |
| 7,129,378 B2 | 10/2006 | Han et al. |
| 7,256,297 B2 | 8/2007 | Senanayake et al. |
| 8,222,264 B2 | 7/2012 | Fuchs et al. |
| 8,426,607 B2 | 4/2013 | Fuchs et al. |
| 8,450,308 B2 | 5/2013 | Dillard et al. |
| 8,633,212 B2 | 1/2014 | Cacatian et al. |
| 8,664,388 B2 | 3/2014 | Fuchs et al. |
| 2013/0053377 A1 | 2/2013 | Dillard et al. |
| 2013/0289050 A1 | 10/2013 | Bukhtiyarov et al. |
| 2013/0317014 A1 | 11/2013 | Dillard et al. |
| 2014/0057927 A1 | 2/2014 | Bukhtiyarov et al. |

FOREIGN PATENT DOCUMENTS

| | | |
|---|---|---|
| CN | 101638399 A | 2/2010 |
| EP | 2042571 A1 | 4/2009 |
| JP | 2007070270 A | 3/2007 |
| WO | 2009007300 A2 | 1/2009 |
| WO | 2009092566 A1 | 7/2009 |
| WO | 2010021680 A2 | 2/2010 |
| WO | 2010043000 A1 | 4/2010 |
| WO | 2010105179 A2 | 9/2010 |
| WO | 2011106414 A1 | 9/2011 |
| WO | 2013134085 A1 | 9/2013 |
| WO | 2013169531 A1 | 11/2013 |
| WO | 2014035860 A1 | 3/2014 |

OTHER PUBLICATIONS

Reichardt, Christian. Classification of Solvents, in Solvents and Solvent Effects in Organic Chemistry, Third Edition, (2002) Wiley-VCH Verlag GmbH & Co. KGaA, Weinheim, FRG. doi: 10.1002/3527601791.ch3.*
Abstract in English for CN 101638399, publication date Feb. 3, 2010.
Abstract in English for JP 2007070270, publication date Mar. 22, 2007.
Booher, R. et al., "Various 5-Substituted and 2,5-Disubstituted 1,3-Dioxanes, a New Class of Analgesic Agents." Journal of Medicinal Chemistry, 1977, vol. 20, No. 7, pp. 885-890.
Gunanathan, C. et al., "Selective Synthesis of Primary Amines Directly from Alcohols and Ammonia." Angewandte Chemie, 2008, vol. 47, No. 45, pp. 8661-8664.
Han, Z. et al., "Enantioselective Synthesis of Diverse Sulfinamides and Sulfinylferrocenes from Phenylglycine-Derived Chiral Sulfinyl Transfer Agent." The Journal of Organic Chemistry, 2011, vol. 76, pp. 5480-5484.

(Continued)

*Primary Examiner* — Golam M M Shameem
*Assistant Examiner* — Laura Daniel
(74) *Attorney, Agent, or Firm* — Michael P. Morris; Atabak R. Royaee

(57) ABSTRACT

This invention relates to methods for making oxetan-3-ylmethanamines having the formula (I) wherein R1? and R2? are as defined herein. The methods of the invention provide the compounds of formula (I) in high yields and under conditions amenable for large-scale commercial production.

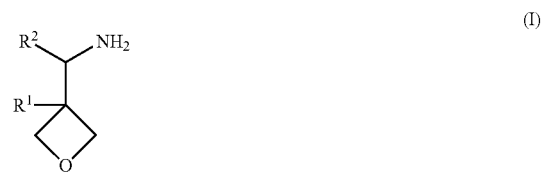

4 Claims, No Drawings

(56) References Cited

OTHER PUBLICATIONS

International Search Report and Written Opinion for PCT/US2013/038969 mailed Aug. 21, 2013.
Kanoh, S. et al., "Double Isomerization of Oxetane Amides to Azetidine Esters with Ring Expansion and Contraction." Journal of Organic Chemistry, 2000, vol. 65, No. 7, pp. 2253-2256.
Mabic, S. et al., "Synthesis of enantiomerically pure ethylenediamines from chiral sulfinimines: a new twist to the Strecker reaction." Tetrahedron, 2001, vol. 57, No. 42, pp. 8861-8866.
Meskini, I. et al., "Crystal Structure of Diethyl[(4chlorophenyl)(dibenzylamino)methyl]propanedioate." Journal of Chemical Crystallography, 2010, vol. 40, No. 4, pp. 391-395.
Meskini, I. et al., "Diethyl 2-{(dibenzylamino) [4-(trifluoro-methyl)phenyl]methyl}malonate." Acta Crystallographica Section E, Structure Reports Online, 2010, vol. E66, pp. o961-o962.
Nemoto, H. et al., "Highly diastereoselective nucleophilic addition reactions of masked acyl cyanide reagents to tert-butanesulfiminides." Tetrahedron:Asymmetry, 2007, vol. 18, No. 3, pp. 383-389.
Nishimura, T. et al., "Chemoselective isomerization of amide-substituted oxetanes with Lewis acid to give oxazine derivatives or bicyclic amide acetals." Chemical Communications, 1998, pp. 43-44.
Reeves, J. et al., "Carbamoyl Anion Addition to N-Sulfinyl Imines: Highly Diastereoselective Synthesis of a-Amino Amides." Journal of the American Chemical Society, 2013, vol. 135, No. 15, pp. 5565-5568.
Uneme, H. et al., "Synthesis and Biological Activity of the Functional Derivatives of 3- and 4-(Dimethyl-aminomethyl)-1,2-dithiolanes." Bioscience, Biotechnology, and Biochemistry, 1992, vol. 56, No. 10, pp. 1623-1631.
Wnuk, S. et al., "Rearrangement of Nitropyridylidenemalonate 1-Oxides. A Novel Method for the Synthesis of Aminopyridine Derivatives." Tetrahedron, 2000, vol. 56, No. 39, pp. 7667-7671.
Xu, Q. et al., "SmI2-Mediated Carbon-Carbon Bond Fragmentation in a-Aminomethyl Malonates." Organic Letters, 2009, vol. 11, No. 18, pp. 4136-4138.
Atkinson, R.O., "Mannich Bases of Acylaminomalonates and a synthesis of DL-aspartic acid." Journal of the Themical Society,1952, pp. 3317-3318.
International Search Report and Written Opinion for PCT/US2013/068488 mailed May 15, 2014.
Meskini, I. et al., "Synthesis, characterization and corrdination chemistry of substituted β-amino dicarbonyls." Journal of Saudi Chemical Society, 2012, vol. 16, No. 2, pp. 161-173.
Xu, Q. et al., "SmI2-Mediated Carbon-Carbon Bond Fragmentation in a-Aminomethyl Malonates." Organic Letters, Supporting Information, 2009, vol. 11, No. 18, pp. S1-S29.

\* cited by examiner

METHODS FOR MAKING OXETAN-3-YLMETHANAMINES

BACKGROUND OF THE INVENTION

This invention relates to novel methods for making oxetan-3-ylmethanamines and intermediates useful for making the oxetan-3-ylmethanamines.

BACKGROUND INFORMATION

Oxetan-3-ylmethanamines (which have the structure shown below) are useful for carrying out amination reactions where it is desired to introduce an oxetan-3-ylmethanamino group onto an organic moiety (see, e.g., WO2011147951, WO2011063159 and WO2011/153509):

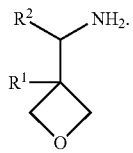

Some oxetan-3-ylmethanamines of the structure shown above where $R^1$ is hydrogen, fluorine, or alkyl; and $R^2$ is hydrogen or alkyl are available in laboratory-scale quantities and/or can be made by published methods.

C. Gunanathan et al., *Angew. Chem. Int. Ed.* 47:8661 (2008)) describes a method of making (3-methyloxetan-3-yl)methanamine by amination of (3-methyloxetan-3-yl)methanol with ammonia (7.5 atmospheres) in the presence of a ruthenium catalyst.

CN101638399 describes a method of making (3-methyloxetan-3-yl)methanamine by reacting 3-(chloromethyl)-3-methyloxetane with liquid ammonia in a high pressure reactor.

JP 2007070270 describes a method of making (3-ethyloxetan-3-yl)methanamine by reacting (3-ethyloxetan-3-yl)methanol with sulfonyl chloride (e.g., methane sulfonyl chloride, p-toluenesulfonyl chloride) followed by reaction with ammonia.

Oxetan-3-ylmethanamine (where $R^1$ and $R^2$ are both hydrogen) is available in laboratory-scale quantities. However, the inventors are not aware of any published methods for making this compound, let alone a method amenable for large-scale commercial production.

BRIEF SUMMARY OF THE INVENTION

The invention relates to novel methods of making the compounds of formula (I) as defined below. The invention also relates to intermediates useful for making the compounds of formula (I).

The Processes of the Invention

The present invention relates to a method of making the compound of formula (I) and methods of making intermediates useful for making the compounds of formula (I):

(I)

the process comprising the following steps:
1) reacting the compound of formula (V):

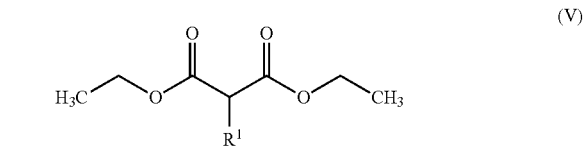

(V)

with a compound of formula (VI):

(VI)

and a compound of formula (VII):

(VII)

followed by reaction with acetic acid to provide the compound of formula (IV):

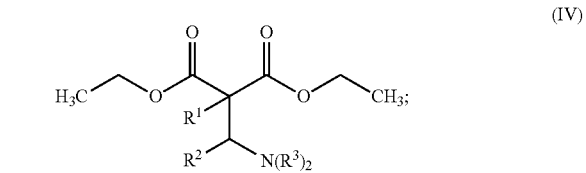

(IV)

2) reacting the compound of formula (IV) from step 1) above with a reducing reagent to provide the compound of formula (III):

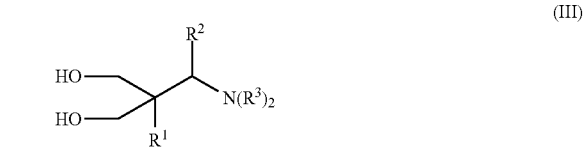

(III)

3) reacting the compound of formula (III) from step 2) above with an arylsulfonyl chloride and a deprotonating reagent to provide the compound of formula (II);

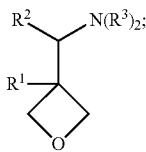

(II)

and 4) reacting the compound of formula (II) from step 3) above with hydrogen gas in the presence of a transition metal catalyst to provide the compound of formula (I), wherein:

$R^1$ is selected from hydrogen, —$(C_1-C_6)$alkyl, —$CF_3$, —$(C_3-C_6)$carbocyclyl, and phenyl;

$R^2$ is selected from hydrogen, —$(C_1-C_6)$alkyl, —$CF_3$, —$(C_3-C_6)$carbocyclyl, and phenyl;

wherein at least one of $R^1$ and $R^2$ is hydrogen; and each $R^3$ is independently selected from phenylmethyl (i.e., benzyl), 4-methoxyphenylmethyl, 1-naphthylmethyl, and diphenylmethyl.

In another embodiment, the invention relates to a method of making the compound of formula (I) according to the embodiment immediately above, wherein $R^1$ and $R^2$ are each independently selected from selected from hydrogen and —$(C_1-C_6)$alkyl.

In another embodiment, the invention relates to a method of making the compound of formula (I) according to any one of the preceding embodiments, wherein $R^1$ and $R^2$ are hydrogen.

In another embodiment, the invention relates to a method of making the compound of formula (I) according to any one of the preceding embodiments, wherein each $R^3$ is phenylmethyl.

In another embodiment, the invention relates to a method of making the compound of formula (I) according to any one of the preceding embodiments, wherein the arylsulfonyl chloride is p-toluenesulfonyl chloride and the deprotonating agent is lithium bis(trimethylsilyl)amide.

In another embodiment, the invention relates to a method of making the compound of formula (I) according to any one of the preceding embodiments, wherein the transition metal catalyst is palladium supported on carbon.

In another embodiment, the invention relates to a method of making the compound of formula (I) according to any one of the preceding embodiments wherein the wherein the reducing reagent is sodium bis(2-methoxyethoxy)aluminum.

The present invention also relates to methods of making intermediates useful for making the compounds of formula (I).

In another embodiment, the invention relates to a method of making the compound of formula (I):

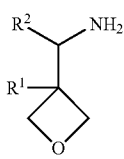

(I)

the process comprising:
reacting a compound of formula (II):

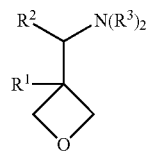

(II)

with hydrogen gas in the presence of a transition metal catalyst to provide the compound of formula (I);

wherein:

$R^1$ is selected from hydrogen, —$(C_1-C_6)$alkyl, —$CF_3$, —$(C_3-C_6)$carbocyclyl, and phenyl;

$R^2$ is selected from hydrogen, —$(C_1-C_6)$alkyl, —$CF_3$, —$(C_3-C_6)$carbocyclyl, and phenyl;

wherein at least one of $R^1$ and $R^2$ is hydrogen; and each $R^3$ is independently selected from phenylmethyl, 4-methoxyphenylmethyl, 1-naphthylmethyl, and diphenylmethyl.

In another embodiment, the invention relates to a method of making the compound of formula (I) according to the embodiment immediately above, wherein $R^1$ is selected from hydrogen and —$(C_1-C_6)$alkyl.

In another embodiment, the invention relates to a method of making the compound of formula (I) according to any one of the preceding embodiments, wherein $R^1$ is hydrogen.

In another embodiment, the invention relates to a method of making the compound of formula (I) according any one of the preceding embodiments, wherein $R^2$ is selected from selected from hydrogen and —$(C_1-C_6)$alkyl.

In another embodiment, the invention relates to a method of making the compound of formula (I) according the broadest embodiment above, wherein $R^2$ is hydrogen.

In another embodiment, the invention relates to a method of making the compound of formula (I) according to any one of the preceding embodiments, wherein each $R^3$ is independently selected from phenylmethyl and 4-methoxyphenylmethyl.

In another embodiment, the invention relates to a method of making the compound of formula (I) according to any one of the preceding embodiments, wherein each $R^3$ is phenylmethyl.

In another embodiment, the invention relates to a method of making the compound of formula (I) according to the broadest embodiment above, wherein $R^1$ and $R^2$ are hydrogen; and $R^3$ is phenylmethyl.

In another embodiment, the invention relates to a method of making the compound of formula (I) according to any one of the preceding embodiments, wherein the transition metal catalyst is palladium supported on carbon.

In another embodiment, the invention relates to a method of making the compound of formula (II):

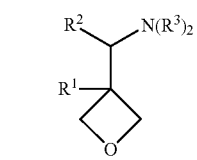

(II)

the process comprising:
reacting a compound of formula (III):

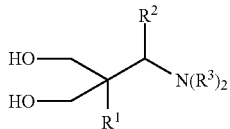

(III)

with an arylsulfonyl chloride and a deprotonating reagent to provide the compound of formula (II);
wherein:
$R^1$ is selected from hydrogen, —($C_1$-$C_6$)alkyl, —$CF_3$, —($C_3$-$C_6$)carbocyclyl, and phenyl;
$R^2$ is selected from hydrogen, —($C_1$-$C_6$)alkyl, —$CF_3$, —($C_3$-$C_6$)carbocyclyl, and phenyl;
wherein at least one of $R^1$ and $R^2$ is hydrogen; and
each $R^3$ is independently selected from phenylmethyl, 4-methoxyphenylmethyl, 1-naphthylmethyl, and diphenylmethyl.

In another embodiment, the invention relates to a method of making the compound of formula (II) according to the embodiment immediately above, wherein $R^1$ is selected from hydrogen and —($C_1$-$C_6$)alkyl.

In another embodiment, the invention relates to a method of making the compound of formula (II) according to any one of the preceding embodiments, wherein $R^1$ is hydrogen.

In another embodiment, the invention relates to a method of making the compound of formula (II) according to any one of the preceding embodiments, wherein $R^2$ is selected from selected from hydrogen and —($C_1$-$C_6$)alkyl.

In another embodiment, the invention relates to a method of making the compound of formula (II) according to any one of the preceding embodiments, wherein $R^2$ is hydrogen.

In another embodiment, the invention relates to a method of making the compound of formula (II) according to any one of the preceding embodiments, wherein each $R^3$ is independently selected from phenylmethyl and 4-methoxyphenylmethyl.

In another embodiment, the invention relates to a method of making the compound of formula (II) according to any one of the preceding embodiments, wherein each $R^3$ is phenylmethyl.

In another embodiment, the invention relates to a method of making the compound of formula (II) according to any one of the preceding embodiments, wherein the deprotonating reagent is a metal amide or a metal alkyl.

In another embodiment, the invention relates to a method of making the compound of formula (II) according to any one of the preceding embodiments, wherein the deprotonating reagent is a metal amide which is lithium bis(trimethylsilyl)amide.

In another embodiment, the invention relates to a method of making the compound of formula (II) according to any one of the preceding embodiments except the embodiment immediately above, wherein the deprotonating reagent is a metal alkyl which is a lithium alkyl selected from methyllithium, ethyllithium, n-propyllithium, sec-propyllithium, n-butyllithium, sec-butyllithium, iso-butyllithium, and tert-butyllithium.

In another embodiment, the invention relates to a method of making the compound of formula (II) according to one of the preceding embodiments, wherein the arylsulfonyl chloride is selected from p-toluenesulfonyl chloride (TsCl), 2,4,6-trimethylbenzenesulfonyl chloride and 2,4,6-triisopropylbenzenesulfonyl chloride.

In another embodiment, the invention relates to a method of making the compound of formula (II) according to the broadest embodiment above, wherein the deprotonating reagent is lithium bis(trimethylsilyl)amide and the arylsulfonyl chloride is p-toluenesulfonyl chloride.

In another embodiment, the invention relates to a method of making the compound of formula (II) according to the embodiment immediately above, wherein $R^1$ and $R^2$ are hydrogen; $R^3$ is phenylmethyl; the deprotonating reagent is lithium bis(trimethylsilyl)amide; and the arylsulfonyl chloride is p-toluenesulfonyl chloride.

In another embodiment, the invention relates to a method of making the compound of formula (II) according to any one of the preceding embodiments, further comprising the step of adding a salt-forming acid to the compound of formula (II) to provide a salt adduct of the compound of formula (II).

In another embodiment, the invention relates to a method of making the compound of formula (II) according to the embodiment immediately above, further comprising the step of adding a base to the salt adduct of the compound of formula (II) to provide the compound of formula (II) in free-base form.

In another embodiment, the invention relates to a method of making the compound of formula (II) according to any one of the two embodiments immediately above, wherein the salt-forming acid is oxalic acid.

In another embodiment, the invention relates to a method of making the compound of formula (III):

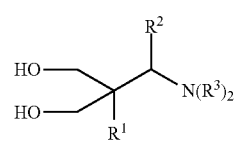

(III)

the process comprising:
reacting a compound of formula (IV):

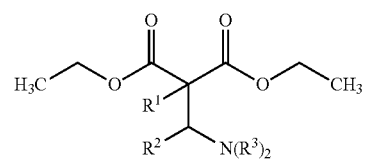

(IV)

with a reducing reagent to provide the compound of formula (III),
wherein:
$R^1$ is selected from hydrogen, —($C_1$-$C_6$)alkyl, —$CF_3$, —($C_3$-$C_6$)carbocyclyl, and phenyl;
$R^2$ is selected from hydrogen, —($C_1$-$C_6$)alkyl, —$CF_3$, —($C_3$-$C_6$)carbocyclyl, and phenyl;
wherein at least one of $R^1$ and $R^2$ is hydrogen; and
each $R^3$ is independently selected from phenylmethyl, 4-methoxyphenylmethyl, 1-naphthylmethyl, and diphenylmethyl.

In another embodiment, the invention relates to a method of making the compound of formula (III) according to the embodiment immediately above, wherein $R^1$ is selected from hydrogen and $—(C_1-C_6)$alkyl.

In another embodiment, the invention relates to a method of making the compound of formula (III) according to any one of the preceding embodiments, wherein $R^1$ is hydrogen.

In another embodiment, the invention relates to a method of making the compound of formula (III) according to any one of the preceding embodiments, wherein $R^2$ is selected from hydrogen and $—(C_1-C_6)$alkyl.

In another embodiment, the invention relates to a method of making the compound of formula (III) according to any one of the preceding embodiments, wherein $R^2$ is hydrogen.

In another embodiment, the invention relates to a method of making the compound of formula (III) according to any one of the preceding embodiments, wherein $R^3$ is phenylmethyl.

In another embodiment, the invention relates to a method of making the compound of formula (III) according to the broadest embodiment above, wherein $R^1$ and $R^2$ are hydrogen; and $R^3$ is phenylmethyl.

In another embodiment, the invention relates to a method of making the compound of formula (III) according to the broadest embodiment above, wherein the reducing reagent is sodium bis(2-methoxyethoxy)aluminum dihydride.

In another embodiment, the invention relates to a method of making the compound of formula (IV):

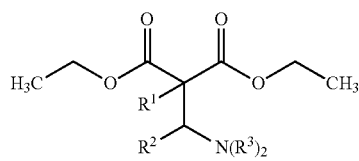

(IV)

the process comprising:
reacting the compound of formula (V):

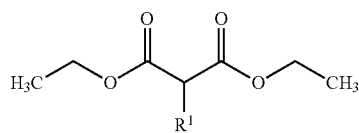

(V)

with a compound of formula (VI):

(VI)

and a compound of formula (VII):

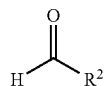

(VII)

followed by reaction with acetic acid to provide the compound of formula (IV),
wherein:
$R^1$ is selected from hydrogen, $—(C_1-C_6)$alkyl, $—CF_3$, $—(C_3-C_6)$carbocyclyl, and phenyl;
$R^2$ is selected from hydrogen, $—(C_1-C_6)$alkyl, $—CF_3$, $—(C_3-C_6)$carbocyclyl, and phenyl;
wherein at least one of $R^1$ and $R^2$ is hydrogen; and each $R^3$ is independently selected from phenylmethyl, 4-methoxyphenylmethyl, 1-naphthylmethyl, and diphenylmethyl.

In another embodiment, the invention relates to a method of making the compound of formula (IV) according to embodiment immediately above wherein $R^1$ is selected from hydrogen and $—(C_1-C_6)$alkyl.

In another embodiment, the invention relates to a method of making the compound of formula (IV) according to any one of the preceding embodiments, wherein $R^1$ is hydrogen.

In another embodiment, the invention relates to a method of making the compound of formula (IV) according to any one of the preceding embodiments, wherein $R^2$ is selected from hydrogen and $—(C_1-C_6)$alkyl.

In another embodiment, the invention relates to a method of making the compound of formula (IV) according to any one of the preceding embodiments, wherein $R^2$ is hydrogen.

In another embodiment, the invention relates to a method of making the compound of formula (IV) according to one of the preceding embodiments, wherein each $R^3$ is independently selected from phenylmethyl and 4-methoxyphenylmethyl.

In another embodiment, the invention relates to a method of making the compound of formula (IV) according to any one of the preceding embodiments, wherein each $R^3$ is phenylmethyl.

In another embodiment, the invention relates to a method of making the compound of formula (IV) according to the broadest embodiment above, wherein $R^1$ and $R^2$ are hydrogen; and $R^3$ is phenylmethyl.

The Compounds of the Invention

As noted above, another aspect of the invention relates to novel intermediates useful for making the compound of formula (I).

In one embodiment, the invention relates to a compound of formula (4):

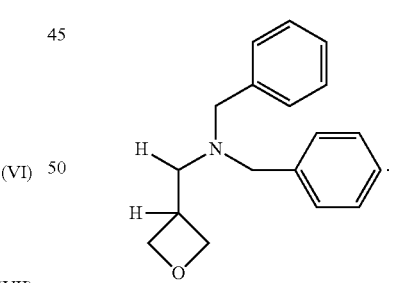

4 and acid addition salts thereof.

In another embodiment, the invention relates to a compound of formula (4) which is an acid addition salt of oxalic acid.

In another embodiment, the invention relates to a compound of formula (4) which is an acid addition salt of oxalic acid, wherein the molar ratio of the compound of formula (4) to oxalic acid is 1:1.

In another embodiment, the invention relates to a compound of formula (4) in the form of a free base.

In another embodiment, the invention relates to a compound of formula (3):

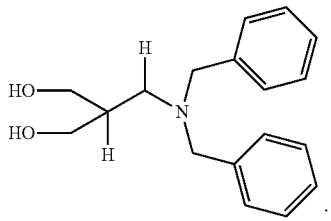

In another embodiment, the invention relates to a compound of formula (2):

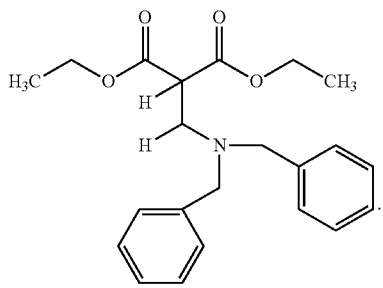

Further aspects of the invention are described below.

DETAILED DESCRIPTION OF THE INVENTION

All terms as used herein in this specification, unless otherwise stated, shall be understood in their ordinary meaning as known in the art. Other more specific definitions are as follows:
AcOH=acetic acid
EtOH=ethanol
KOH=potassium hydroxide
LiN(TMS)$_2$=lithium bis(trimethylsilyl)amide
MeOH=methanol
MTBE—methyl tert-butyl ether
NaOH=sodium hydroxide
Red-Al=sodium bis(2-methoxyethoxy)aluminum dihydride
THF=tetrahydrofuran
TsCl=p-toluenesulfonyl chloride The term "(C$_1$-C$_6$)alkyl" refers to branched and unbranched alkyl groups having from 1 to 6 carbon atoms. Examples of —(C$_1$-C$_6$)alkyls include methyl, ethyl, n-propyl, isopropyl, n-butyl, sec-butyl, isobutyl, tert-butyl, n-pentane, iso-pentyl, neopentyl, n-hexane, iso-hexanes (e.g., 2-methylpentyl, 3-methylpentyl, 2,3-dimethylbutyl, and 2,2-dimethylbutyl). It will be understood that any chemically feasible carbon atom of the (C$_1$-C$_6$)alkyl group can be the point of attachment to another group or moiety.

The term "(C$_3$-C$_6$)carbocycloalkyl" refers to a nonaromatic 3- to 6-membered monocyclic carbocyclic radical. Examples of "(C$_3$-C$_6$)carbocycloalkyls" include cyclopropyl, cyclobutyl, cyclohexyl, cyclopentyl, and cyclohexyl.

The term "halo" or "halogen" refers to fluoro, chloro, bromo or iodo.

The symbol

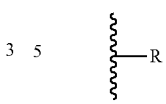

means point of attachment of a group R to a moiety.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

Certain compounds used in the processes of the invention may exist as salts formed from inorganic and organic acids. Such acids may be employed in preparing and/or isolating certain intermediates. For convenience, such acids are referred to herein as "salt-forming acids" and the salts formed from such salt-forming acids are referred to herein as "salt adducts." A non-limiting example of a useful salt-forming acid is oxalic acid.

As noted above, the invention relates in one embodiment to methods of making the compounds of formula (I), (II), (III), and (IV). Methods of making the compounds of formula (I), (II), (III), and (IV) according to the invention are described below where the groups R$^1$, R$^2$ and R$^3$ are as defined above.

A nonlimiting method for making the compound of formula (I) according to the invention is depicted in Scheme 1 below.

Scheme 1

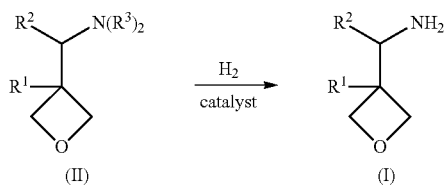

As depicted in Scheme 1, the compound of formula (II) is reacted with hydrogen in the presence of a transition metal catalyst, e.g., palladium supported on carbon. The reaction is typically carried out by charging the compound of formula (II), the transition metal catalyst and, optionally, a solvent (e.g., methanol) into suitable reaction vessel. The reaction vessel is then pressurized with hydrogen gas for a suitable time and temperature sufficient to provide the compound of formula (I). The hydrogen overpressure can vary. Typically, the hydrogen is added in amount to increase the pressure in the reaction vessel from about 1 to about 100 atm; from about 1 to about 50 atm; from about 1 to about 20 atm; or from about 10 to about 20 atm. The reaction is carried out for a time and temperature sufficient to provide the compound of formula (I), typically for about 0.5 to about 100 hours and at a temperature of from about 0° C. to about 100° C. The reaction is deemed to be complete when no more hydrogen gas is consumed.

A nonlimiting method for making the compound of formula (II) according to the invention is depicted in Scheme 2 below.

Scheme 2

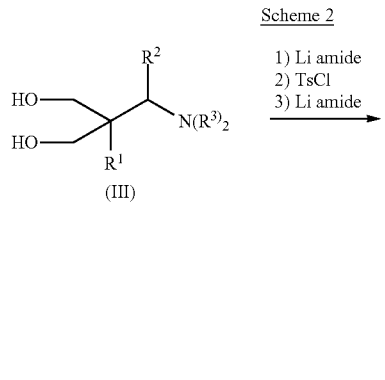

As depicted in Scheme 2, the compound of formula (III) is reacted first with a deprotonating reagent such as a metal amide (for example, a lithium amide) followed by reaction with p-toluenesuflonyl chloride (TsCl) or another arylsulfonyl chloride such as 2,4,6-trimethylbenzenesulfonyl chloride or 2,4,6-triisopropylbenzenesulfonyl chloride. The resulting admixture is then treated with additional metal amide to provide the compound of formula (II). The reaction is carried out under anhydrous conditions using inert, aprotic solvent (e.g., tetrahydrofuran, ether, hexane, and heptane). The addition of the metal amide and p-toluenesuflonyl chloride is generally carried at reduced temperature, for example, from about 0° C. to about 20° C. The rate of addition of the metal amide and p-toluenesuflonyl chloride is generally such that the reaction temperature can be maintained within the desired range (for example, from about 0° C. to about 10° C.). Once addition of the all reagents is complete, the reaction mixture is stirred for a time and at a temperature sufficient to provide the compound of formula (II), typically for about 1 to 24 hours and at a temperature of from about 25° C. to about the refluxing temperature of the solvent. In the process depicted in Steps 1) and 2) in Scheme 1, the metal amide can, if desired, be replaced with a metal alkyl (e.g., n-butyl lithium).

A nonlimiting method for making the compound of formula (III) according to the invention is depicted in Scheme 3 below.

Scheme 3

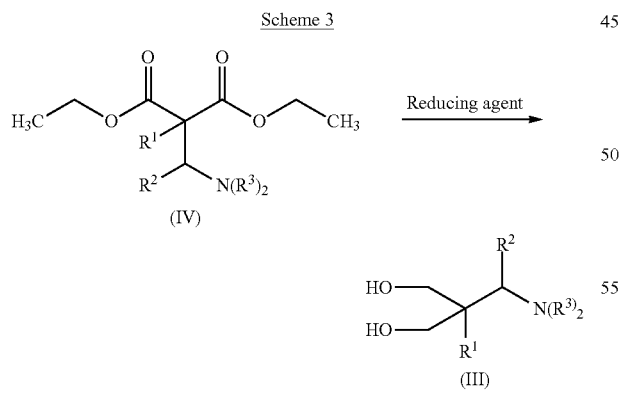

As depicted in Scheme 3, the compound of formula (IV) is reacted with a reducing reagent to provide the compound of formula (III). Nonlimiting examples of reducing reagent useful for the described process include aluminum hydrides such as sodium bis(2-methoxyethoxy)aluminum dihydride and lithium bis(2-methoxyethoxy)aluminum dihydride. The reaction is carried out under anhydrous conditions using inert, aprotic solvent (e.g., toluene). The reaction is carried out at a temperature and time sufficient to provide the compound of formula (III), typically from about 0.5 hours to about 100 hours and at a temperature of from about 0° C. to about the refluxing temperature of the solvent.

A nonlimiting method for making the compound of formula (IV) according to the invention is depicted in Scheme 4 below.

Scheme 4

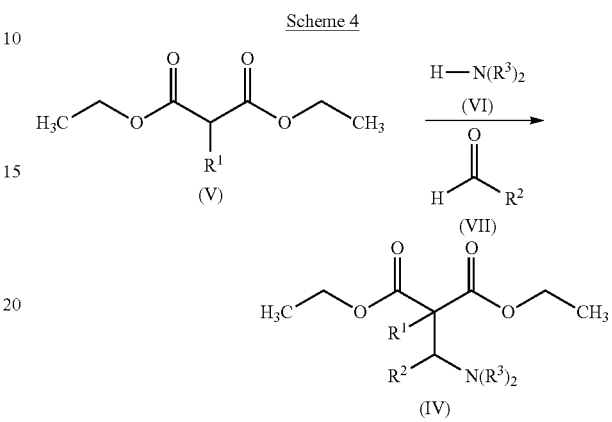

As depicted in Scheme 4, the compound of formula (V) is reacted with the compound of formula (VI) and the compound of formula (VII) to provide the compound of formula (IV). Typically, the compound formula (VI) is added to a reaction vessel containing the compound of formula (V) and suitable solvent (e.g., tetrahydrofuran). The resulting admixture is then treated with a solution of the compound of formula (VII) (e.g., aqueous solution) at a rate sufficient to maintain a temperature of not more than about 25° C. The resulting admixture is then treated with acetic acid and heated for a time and at a temperature sufficient to provide the compound of formula (IV), typically from about 0.5 hours to about 100 hours and at a temperature of from about 40° to about the refluxing temperature of the mixture. Alternatively, the compound of formula (IV) may be prepared according to known methods (see, e.g., Meskini, I. et al., "Crystal Structure of Diethyl [(4-Chlorophenyl)(dibenzylamino)methyl] propanedioate," *Journal of Chemical Crystallography* 40(4), 391-395 (2010); and Meskini, I. et al., "Diethyl 2-{(dibenzylamino)[4-(trifluoromethyl)phenyl]methyl}malonate," *Acta Crystallographica, Section E: Structure Reports Online* E66 (4), o961-o962 (2010).

EXAMPLES

Reaction monitoring was performed by either TLC or reverse phase HPLC. Compound purity was determined by ¹H NMR assay using dimethyl fumarate as an internal standard.

Example 1

Preparation of oxetan-3-ylmethanamine (1)

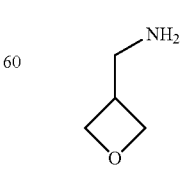

Compound 1 can be prepared by the methods described below.

Step 1. Preparation of diethyl 2-((dibenzylamino)methyl)malonate (2)

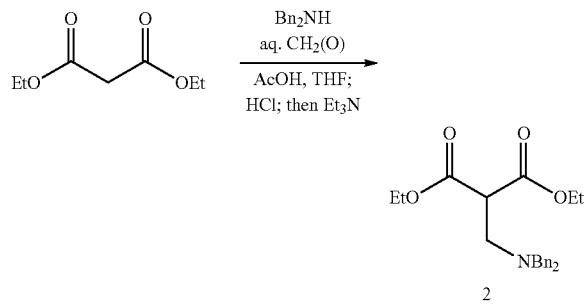

A flask is charged with diethyl malonate (250.0 g, 1.56 mol), THF (470 mL), and dibenzylamine (315.8 mL, 1.64 mol). Formaldehyde (122.3 mL, 1.64 mol, 37% aqueous solution) is added at a rate sufficient to maintain the batch at a temperature below 25° C. The reaction mixture is stirred at about 25° C. for 15 minutes, and then treated with acetic acid (89.4 mL, 1.56 mol) over 10 minutes. The reaction mixture is stirred at about 25° C. for 1 hour, and then heated at 65° C. for 2 hours. The reaction mixture is cooled to about 25° C. Toluene (1.3 L) and water (1 L) are added, the batch is stirred, and the aqueous layer is removed. The batch is washed again with water (1 L). The batch is then concentrated by distillation under vacuum at 50-55° C. to an oil. To this oil is added 2-methyltetrahydrofuran (1.2 L), and the solution is cooled to about 0° C. A solution of HCl (300 mL, 1.2 mol, 4M) in dioxane is added at a rate to sufficient to maintain the temperature below 12° C. The batch is warmed at about 25° C. over 30 minutes, and stirred at this temperature for 4 hours. The solid is filtered and washed with 2-methyltetrahydrofuran and dried under vacuum at 30° C. to provide the HCl salt of 2 as a white solid. Yield: 443.0 g, 63.3%. Purity 90.6 wt. %.

Preparation of free base form of 2: The HCl salt of 2 (19.5 g, 48.0 mmol) is suspended in water (100 mL) and toluene (100 mL). To the resultant slurry is added Et$_3$N (7.4 mL, 52.8 mmol), and the mixture is stirred at about 25° C. for 30 minutes. The aqueous phase is removed, and the organic phase is concentrated by distillation under vacuum at 50-55° C. to an oil. Yield: 27.4 g, 99.2% yield; Purity: 64.2 wt. %

Step 2. Preparation of 2-((dibenzylamino)methyl)propane-1,3-diol (3)

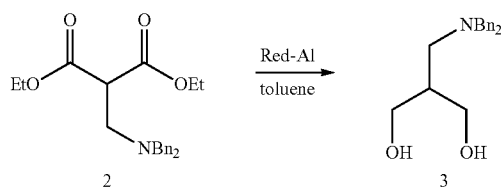

A flask is charged with toluene (160 mL) and sodium bis(2-methoxyethoxy)aluminum dihydride (Red-Al, 137.9 g, 443.4 mmol, 65 wt. % in toluene). The solution is heated to 35° C. and treated with a solution of 2 (54.6 g, 369.5 mmol) in toluene (110 mL) at a rate sufficient to maintain the reaction temperature between 35-42° C. The reaction is stirred while cooling gradually at about 30° C. for 2 hours. The reaction is further cooled to 5° C. and quenched with ethyl acetate (10.3 mL) followed by 1.85N aqueous NaOH solution (176 mL), and the layers are separated. The organic phase is treated with a solution of sodium potassium tartrate (13.65 g) in water (112 mL), and the mixture is heated at 50° C. for about 15 minutes. After cooling at about 25° C., the layers are separated. The organic phase is washed with water (180 mL), and then concentrated by distillation under vacuum at about 50-55° C. to an oil. Toluene (30 mL) is added and the resultant solution is seeded with crystals of 3 (see below) and stirred at about 25° C. for 1 hour. At this point a thick slurry is obtained. Heptane (250 mL) is added dropwise over 30 minutes, stirred an additional 2 hours, and filtered. The solid is washed with heptane and dried under vacuum to provide 3 as a white solid. Yield: 30.4 g, 69.8% yield: Purity: 96.8 wt. %.

Preparation of seed crystals of 3: An initial batch of seed crystals of compound 3 are prepared using the procedure described above except that the crystallization of the toluene solution is carried out without any seeding.

Step 3. Preparation of N,N-dibenzyl-1-(oxetan-3-yl)methanamine (4)

The title compound can be prepared by either Method 1 or Method 2 described below.
Method 1:

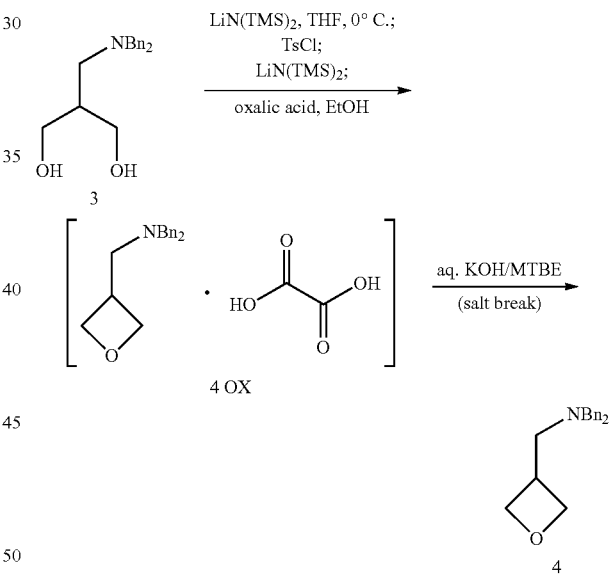

A flask is charged with 3 (60.0 g, 0.191 mol, 91.0 wt. %) and THF (720 mL). The resultant solution is cooled to 0° C. and treated with n-BuLi (75.5 mL, 0.201 mol, 2.66 M in hexanes) at a rate sufficient to keep the temperature of the mixture between 0-10° C. The reaction mixture is stirred at about 0° C. for 30 minutes. A solution of p-toluenesulfonyl chloride (36.5 g, 0.191 mol) in THF (180 mL) is then added at a rate to keep the temperature of the mixture between 0-10° C. The reaction mixture is stirred at about 0° C. for 30 minutes. The reaction is then treated with n-BuLi (75.5 mL, 0.201 mol, 2.66 M in hexanes) at a rate to keep the temperature of the mixture between 0-10° C. The reaction mixture is then heated to about 45° C. and held at this temperature for 1 hour. The reaction mixture is cooled to about 25° C. and treated with a solution of aqueous 0.5M NaOH (400 mL), and the THF and hexanes are distilled off at about 35° C. under vacuum. Methyl tert-butyl ether (480 mL) is added, and the aqueous layer is removed. The product solution is concentrated by distillation at 35° C. under vacuum to an oil. Ethanol (200 mL) is added, followed by a solution of oxalic acid dihydrate (19.3 g, 0.153 mol) in ethanol (150 mL). The reaction mixture is stirred to about 25° C. for about 20 hours. The solids are collected by filtration, washed with methyl tert-butyl ether/ethanol (2:1 v/v) and methyl tert-butyl ether, and dried under vacuum to provide 36.3 g of the oxalate adduct of 4 (40×) as a white solid. The solids are stirred with a solution of KOH pellets (19.4 g, 0.294 mol, 85 wt. %) in water (200 mL) and methyl tert-butyl ether (300 mL) for 1 hour. The aqueous layer is removed, and the organic layer is filtered through a 1 cm pad of Celite and concentrated by distillation at 35° C. under vacuum to provide 4 as a light yellow oil. Yield: 27.0 g, 50% yield. Purity: 95 wt. %.

Method 2:

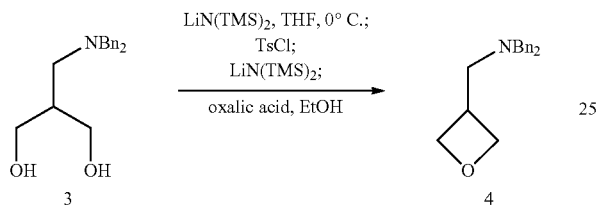

A flask is charged with 3 (2.00 g, 7.01 mmol, 100.0 wt. %) and THF (14 mL). The resultant solution is cooled to 0° C. and treated with LiN(TMS)$_2$ (7.36 mL, 7.36 mmol, 1.00 M in THF) at a rate to keep the temperature of the mixture between 0-5° C. The reaction mixture is stirred at about 0° C. for 30 minutes. A solution of p-toluenesulfonyl chloride (1.36 g, 7.15 mmol) in THF (5 mL) is then added at a rate to keep the temperature of the mixture between 0-5° C. The reaction mixture is stirred at about 0° C. for 30 minutes. The reaction is then treated with LiN(TMS)$_2$ (7.36 mL, 7.36 mmol, 1.00 M in THF) at a rate to keep the temperature of the mixture between 0-5° C. The reaction mixture is then heated to about 55° C. and held at this temperature for 3 hours. The reaction mixture is cooled to about 25° C. and treated with a solution of aqueous 0.5M NaOH (14 mL), and the THF is distilled off at about 35° C. under vacuum. Methyl tert-butyl ether (14 mL) is added, and the aqueous layer is removed. The product solution is concentrated by distillation at 35° C. under vacuum to provide 4 as a light yellow oil. Yield: 2.46 g, 60.0% yield. Purity: 45.7 wt. %.

Step 4. Preparation of oxetan-3-ylmethanamine (1)

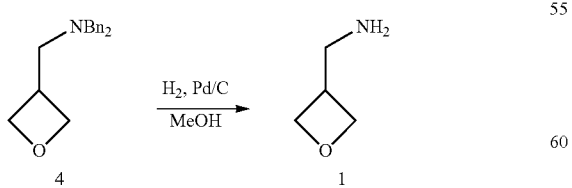

A 600 mL hydrogenator is charged with 4 (30.0 g, 75.0 wt. %, 84.2 mmol), 10 wt. % palladium on carbon (5.0 g, 50 wt. % water), and MeOH (220 mL). The vessel is pressurized with hydrogen to a pressure of 300 psi and hydrogenated at this pressure and 25° C. for 24 hours. The hydrogen is vented and replaced with nitrogen. The reaction mixture is filtered through Celite to remove the catalyst, and the Celite is washed with MeOH. The combined filtrate is concentrated at 25-30° C. under vacuum to provide 1 as a light yellow concentrated solution. Yield: 11.2 g, 85.9% yield. Purity: 56.2 wt. %.

What is claimed is:
1. A method of making the compound of formula (I):

the method comprising the following steps:
1) reacting the compound of formula (V):

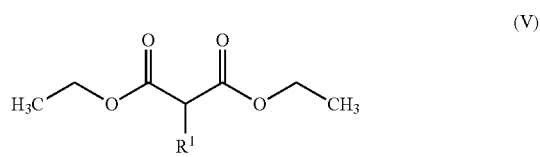

with a compound of formula (VI):

and a compound of formula (VII):

followed by reaction with acetic acid to provide the compound of formula (IV):

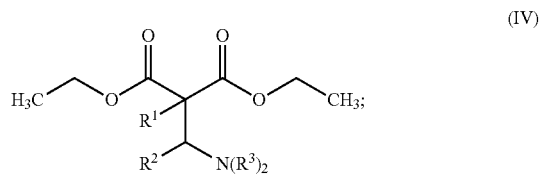

2) reacting the compound of formula (IV) from step 1) above with a reducing reagent to provide the compound of formula (III):

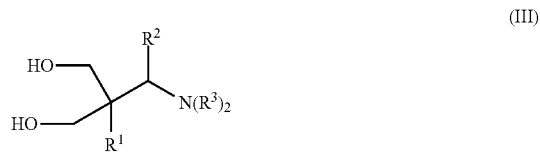

3) reacting the compound of formula (III) from step 2) above with an arylsulfonyl chloride and a deprotonating reagent to provide the compound of formula (II);

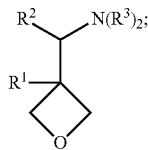
(II)

and 4) reacting the compound of formula (II) from step 3) above with hydrogen gas in the presence of a transition metal catalyst to provide the compound of formula (I), wherein:
R$^1$ is selected from hydrogen, —(C$_1$-C$_6$)alkyl, —CF$_3$, —(C$_3$-C$_6$)carbocyclyl, and phenyl;
R$^2$ is selected from hydrogen, —(C$_1$-C$_6$)alkyl, —CF$_3$, —(C$_3$-C$_6$)carbocyclyl, and phenyl;
wherein at least one of R$^1$ and R$^2$ is hydrogen; and
each R$^3$ is independently selected from phenylmethyl, 4-methoxyphenylmethyl, 1-naphthylmethyl, and diphenylmethyl.

2. A method of making a compound of formula (I):

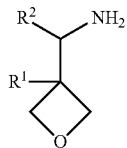
(I)

the process comprising:
reacting a compound of formula (II):

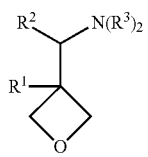
(II)

with hydrogen gas in the presence of a transition metal catalyst to provide the compound of formula (I);
wherein:
R$^1$ is selected from hydrogen, —(C$_1$-C$_6$)alkyl, —CF$_3$, —(C$_3$-C$_6$)carbocyclyl, and phenyl;
R$^2$ is selected from hydrogen, —(C$_1$-C$_6$)alkyl, —CF$_3$, —(C$_3$-C$_6$)carbocyclyl, and phenyl;
wherein at least one of R$^1$ and R$^2$ is hydrogen; and
each R$^3$ is independently selected from phenylmethyl, 4-methoxyphenylmethyl, 1-naphthylmethyl, and diphenylmethyl.

3. A method of making the compound of formula (II):

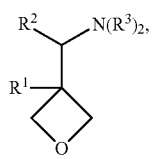
(II)

the process comprising:
reacting a compound of formula (III):

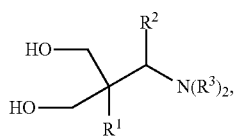
(III)

with an arylsulfonyl chloride and a deprotonating reagent to provide the compound of formula (II),
wherein:
R$^1$ is selected from hydrogen, —(C$_1$-C$_6$)alkyl, —CF$_3$, —(C$_3$-C$_6$)carbocyclyl, and phenyl;
R$^2$ is selected from hydrogen, —(C$_1$-C$_6$)alkyl, —CF$_3$, —(C$_3$-C$_6$)carbocyclyl, and phenyl;
wherein at least one of R$^1$ and R$^2$ is hydrogen; and
each R$^3$ is independently selected from phenylmethyl, 4-methoxyphenylmethyl, 1-naphthylmethyl, and diphenylmethyl.

4. A compound of formula (4):

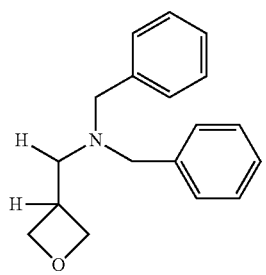
4 and acid addition salts thereof.

* * * * *